(12) United States Patent
Ellman

(10) Patent No.: US 9,028,491 B2
(45) Date of Patent: May 12, 2015

(54) MIS ELECTROSURGICAL HANDPIECE

(76) Inventor: Alan G. Ellman, Oceanside, NY (US)

( * ) Notice: Subject to any disclaimer, the term of this patent is extended or adjusted under 35 U.S.C. 154(b) by 1652 days.

(21) Appl. No.: 12/228,838

(22) Filed: Aug. 18, 2008

(65) Prior Publication Data

US 2010/0042096 A1 Feb. 18, 2010

(51) Int. Cl.
*A61B 18/18* (2006.01)
*A61B 18/04* (2006.01)
*A61B 18/14* (2006.01)
*A61B 17/29* (2006.01)
*A61B 18/00* (2006.01)

(52) U.S. Cl.
CPC ......... A61B 18/1445 (2013.01); *A61B 17/2909* (2013.01); *A61B 2018/00916* (2013.01)

(58) Field of Classification Search
CPC ............... A61B 18/14; A61B 18/12; A61B 2018/1405; A61B 2018/1475; A61B 18/1442; A61B 18/1445; A61B 2018/145; A61B 2018/1462; A61B 2018/126
USPC ............... 606/48, 50–52, 41, 205–207, 32
See application file for complete search history.

(56) References Cited

U.S. PATENT DOCUMENTS

| 4,003,380 | A * | 1/1977 | Wien | 606/51 |
|---|---|---|---|---|
| 4,418,692 | A * | 12/1983 | Guay | 606/42 |
| 4,819,633 | A * | 4/1989 | Bauer et al. | 606/52 |
| 5,258,006 | A * | 11/1993 | Rydell et al. | 606/205 |
| 6,190,386 | B1 * | 2/2001 | Rydell | 606/51 |
| 6,245,070 | B1 * | 6/2001 | Marquis et al. | 606/51 |
| 6,382,968 | B2 * | 5/2002 | Livaditis | 433/32 |
| 6,482,205 | B1 * | 11/2002 | Bonnet | 606/51 |
| 6,524,309 | B1 * | 2/2003 | Watrelot et al. | 606/51 |

* cited by examiner

*Primary Examiner* — Kevin C Sirmons
*Assistant Examiner* — Bradley G Thomas, Jr.

(57) ABSTRACT

An electrosurgical handpiece comprising a squeezable handle connected to extend and retract bipolar electrodes from a rigid tubular member. The bipolar electrodes comprise active separable distal ends and connecting links configured such that when the handle is unsqueezed, the active distal ends protrude from the distal end of the first tubular member and are adjacent one another, and when the handle is fully squeezed, the active distal ends are fully extended outwardly from the first tubular member and separate, and when the handle is relaxed but still partially squeezed, the active distal ends come together and touch first at their extreme ends and then touch over a broader area in a position to grasp tissue for receiving electrosurgical currents.

16 Claims, 2 Drawing Sheets

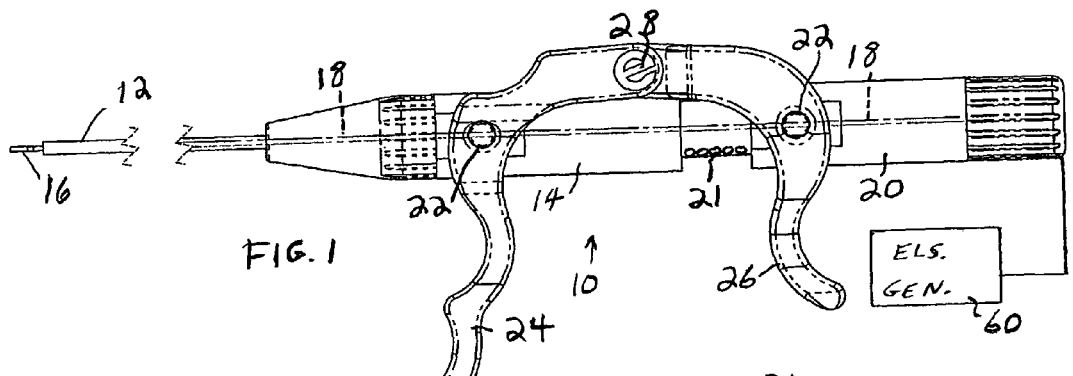
FIG. 1
FIG. 3
FIG. 2
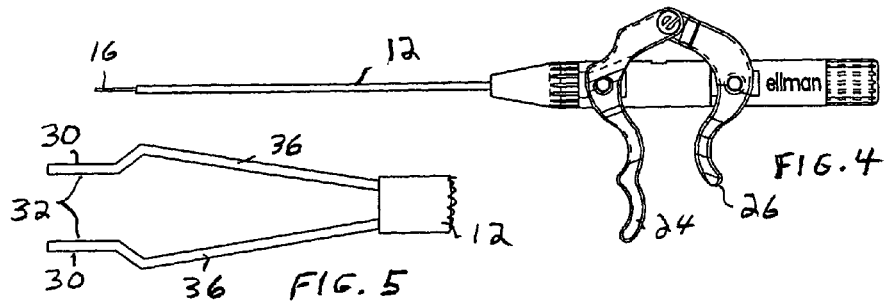
FIG. 4
FIG. 5
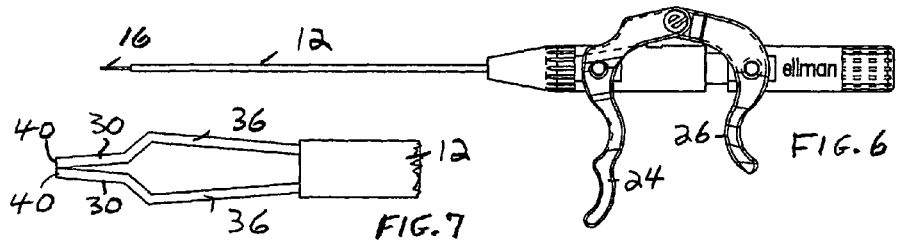
FIG. 6
FIG. 7

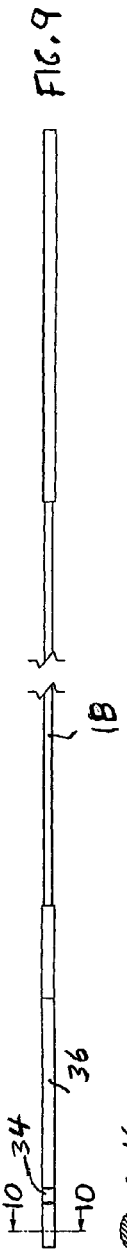
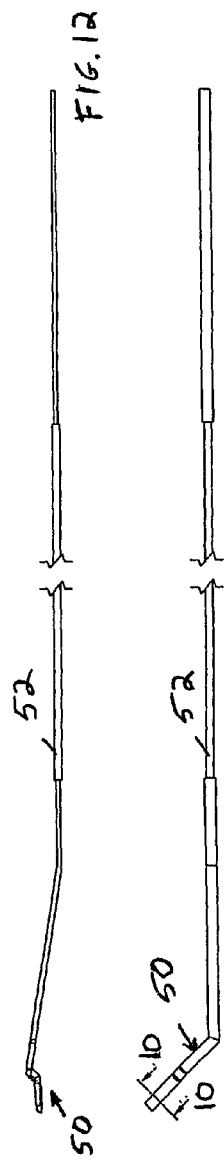
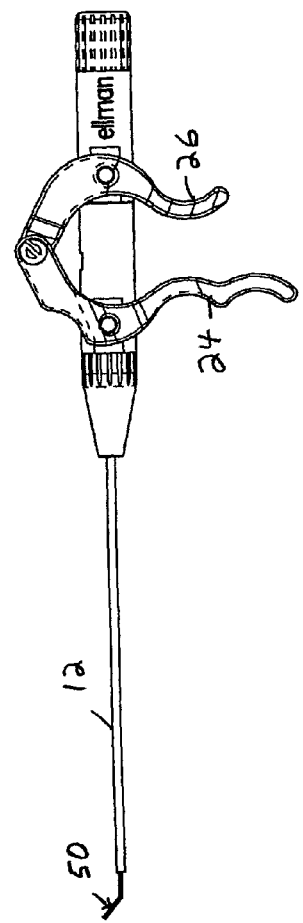

MIS ELECTROSURGICAL HANDPIECE

BACKGROUND OF THE INVENTION

A bipolar electrosurgical handpiece is described in U.S. Pat. No. 6,231,571 and D562,978, the contents of which are herein incorporated by reference, an example of which is known commercially as the Trigger-Flex Bipolar System and is available from Elliquence LLC of Oceanside, N.Y. The handpiece comprises an elongated rigid tube within which is housed extendable electrosurgical electrodes, preferably of the bipolar type. By special construction of the distal end of the electrodes, such as by the use of memory metal, when the handle is squeezed the bipolar electrodes, whose spacing is fixed, are extended from their tube and bent in accordance with the presetting of the memory metal. Typically, such an electrosurgical handpiece is employed with a cannula for minimally invasive surgical (MIS) procedures.

There are certain procedures in which it is desired for the bipolar electrodes to follow a certain path allowing the electrodes to grasp certain tissue before electrosurgical currents are supplied. Examples are general pin-point coagulation in all delicate neurosurgical procedures, transphenoidal surgery, and in certain cases of devascularization of tumors and debulking of lesions/tumors.

SUMMARY OF THE INVENTION

An object of the invention is an improved electrosurgical handpiece for use in performing MIS procedures.

Another object of the invention is an improved electrosurgical handpiece adapted for grasping tissue in a particular fashion.

In accordance with one aspect of our invention, a novel electrosurgical handpiece comprises an elongated rigid tubular member housing extendable bipolar electrodes, with the tubular member configured to fit within and be extended down a standard sized cannula in a MIS procedure. Squeezable handles support the tubular member and are configured such that when the handles are squeezed, the active electrode ends are extended out through the cannula end and opened, i.e., spread apart. When the handles are released, the electrode ends are pulled back into the cannula and forced to close.

A feature of the invention is the configuration of the tips of the bipolar electrode ends, which are formed into flat opposing surfaces, and the relationship of their connecting links to the tubular member. The connecting links are configured such that, as the handles are released, when they first are forced to close as they withdraw into the tubular member, the distal ends of the electrode tips touch first. As they continue withdraw into the tubular member and to close, the flat surfaces are pressed up against one another. This action ensures that any tissue grasped as the tips close is held securely in the tips and not squeezed out.

As another feature of the invention, the electrode tips can be arranged to extend out in a straight line along an extension of the elongated tube axis, or bent off the axis in order to reach tissue portions not readily accessible from a straight line extension.

The housed bipolar electrodes as in the referenced patents and application are electrically active and are capable when energized of applying electrosurgical currents to grasped human tissue with the result that a void or cavity or tunnel can be formed in the tissue or bleeders sealed. Any tissue removed may then be easily aspirated via a suction port connected to the handpiece.

Preferably, radio-frequency (RF) electrosurgical currents, in a frequency range preferably above 3 MHz, with 4 MHz being preferred, are employed. It is believed that 4 MHz radiofrequency energy has been proven to be a self-limiting, minimal penetration energy source capable of precise tissue interaction. Thus, electrosurgical instruments that emit 4 MHz radiofrequency currents will be attractive to spinal or other surgeons needing to produce controlled tissue modulation efficiently and safely. Since lateral heat is typically not a byproduct of 4 MHz RF currents, damage to surrounding tissue can be minimized or avoided.

Thus, a MIS electrosurgical procedure using the novel system components described herein enables physicians to offer to patients a treatment that is efficiently performed, relatively easily learned and thus performed at a significantly reduced price, and with less tissue damage and superior results compared to procedures done with other devices.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals or letters signifying the same or similar components.

BRIEF DESCRIPTION OF THE DRAWINGS

FIG. 1 is an enlarged plan view from the side of one form of electrosurgical handpiece in accordance with the invention in its relaxed position shown schematically connected to an electrosurgical generator;

FIG. 2 is a top view of the electrosurgical handpiece of FIG. 1 also in its relaxed position;

FIG. 3 is an enlarged top view of the protruding electrode ends of the electrosurgical handpiece of FIG. 2 in the relaxed non-squeezed handle position shown in FIG. 1;

FIG. 4 is a side view of the electrosurgical handpiece of FIG. 1 shown in its fully squeezed handle position;

FIG. 5 is an enlarged top view of the protruding electrodes of the electrosurgical handpiece of FIG. 4 in its fully-squeezed position;

FIG. 6 is a side view of the electrosurgical handpiece of FIG. 1 shown in its middle or partially relaxed handle position;

FIG. 7 is an enlarged top view of the protruding electrodes of the electrosurgical handpiece of FIG. 6 in the partially-relaxed handle position;

FIG. 8 is a side view of the electrode and its connecting link for the electrosurgical handpiece of FIG. 1 with a straight electrode;

FIG. 9 is a top view of the electrode and its link of FIG. 8;

FIG. 10 is a cross section along the line 10-10 of FIG. 9.

FIG. 11 is a side view of a variant of the electrosurgical handpiece of FIG. 1 in its squeezed position in which the electrode is angled.

FIG. 12 is a side view of the electrode and its connecting link for the electrosurgical handpiece of FIG. 11 with an angled electrode;

FIG. 13 is a top view of the electrode and its link of FIG. 12;

DETAILED DESCRIPTION OF THE PREFERRED EMBODIMENTS

The present invention is an improvement of the electrosurgical apparatus described in U.S. Pat. No. 6,231,571; D562, 978; and US pending application, Ser. No. 11/799,603, filed May 3, 2007, the contents of which are herein incorporated by reference. In the referenced patents/application, an electrosurgical handpiece is described in which an elongated rigid tube is fixed to the front end handpiece body to which is affixed the front handle portion. Extendable within the rigid tube is an elongated electrode connected to the rear end handpiece body to which is affixed the rear handle portion. When the handles are squeezed, the electrode is extended and bends in a direction preset into the electrode metal. An incorporated compression spring keeps the two body parts apart. The present invention employs the same basic construction except for the configuration of the electrodes so that when extended and retracted they follow a different path.

Referring now to the drawings, an electrosurgical handpiece 10 in accordance with the invention comprises an elongated rigid tube 12 affixed to the front end body section 14. Inside the rigid tube 12 extends connected to active bipolar electrode ends 16 is an elongated link 18 (shown in dashed lines) which in turn is fixed to the rear end body section 20, which telescopes within the front end section 14. Across the two body sections 14, 20, biased apart by an internal spring shown schematically at 21, is pivotably 22 mounted the front 24 and rear 26 handle portions, which also pivotably connect 28 at the top. The handle configuration differs from that disclosed in the pending application in that the handle portions above their pivots to the body are angled closer to the body to improve surgeon visibility of the surgical site.

The handpiece is typically bipolar with two extended electrodes between which the electrosurgical currents are concentrated. One electrode 16 and its extended link 18 is shown in FIGS. 8-10. Its companion electrode (not shown) is a mirror image of the one shown. The right end of the shank is connected to the rear body section 20, so that when the handles are squeezed the electrode end 16 at the left is extended out of the rigid tube 12. A feature of the invention is the configuration of the electrode 16 and its link 18. As shown in FIG. 8, the left end or distal portion 16 has a short straight flat section 30 with facing surfaces 32 of the active electrode ends that are parallel, electrically bare, and in full contact when the handpiece is in its relaxed position, shown in FIG. 3. Back of the distal section 30 the electrode has a short angled section 34 (at about a 45° angle) followed by a longer straight section 36 that extends toward the center axis of the link. As an example, not to be considered limiting, the rigid tube 12 has an inside diameter of about 2.08 mm (0.083 inches), the overall length of the electrode with its link is about 220 mm, the short parallel section 30 in front is about 3 mm long, the following angled short section 34 is about 1.3 mm long, the longer section 36 returning to the axis is about 15 mm long forming an angle of about 9° where it intersects the axis. The thickness of the straight thicker central section of the link is about 0.5 mm. so when the two bipolar electrodes fill the rigid tube, they occupy about ½-⅔ of the internal space. The peak where the short angle section 34 meets the longer straight section 36 is about 3 mm above the electrode axis. As a result of this configuration, when one of the electrode pair 16 is inside the rigid tube 12 in the relaxed position shown in FIG. 3, the longer straight section 36 of each electrode half bears against the inside wall of the rigid tube 20 forcing the flat distal ends 30 together with their facing surfaces 32 in full contact. At that position, about ⅔ of the tapered longer sections 36 are inside the rigid tube 12.

When the handles are fully squeezed as shown in FIGS. 4 and 5, the electrode ends 30 are extended out about ⅘ of the length of the longer sections 36. Due to the closer spacing of the preset tapered sections 36 still remaining inside the rigid tube, the distal ends 30 spread apart but the opposed surfaces 32 due to the geometry still remain essentially parallel. Now, as shown in FIG. 7, as the hand pressure on the handles 24, 26 relaxes, the electrodes 18 due to the internal spring 21 pressure are forced back into the rigid tube 12, and the internal wall pressure on the sections 36 cause the distal ends 30 to approach one another. The configuration of the electrodes are such that the pressure of the rigid tube 12 on the retracting tapered sections 36 forces the extreme electrode ends 40 toward one another faster than the rearward sections with the result that the extreme ends 40 touch first (FIG. 7), before the rest of the front flat sections. In this position, about ½ of the tapered straight sections 36 remain within the rigid tube 12. Then, as the handles are further relaxed, the remaining parts of the front distal section gradually come together until the position shown in FIG. 3 is restored with the front sections again in full contact over their full facing surfaces 32.

To summarize, when the handles are released, the electrode links 18 are pulled back into the rigid tube acting as a cannula and forced to close. But the tips 30, 34 are bent so that when they first begin to close, the extreme ends 40 touch first, and as they continue to close, the flat faces 32 are finally pressed up against one another. This action is extremely important because it allows the surgeon to position the open ends with their extreme tips exactly at the tissue to be grasped and helps to ensure that the tissue is held securely in the tips and not squeezed out during the further closing action.

In the preferred embodiment, the distal end sections 16 have a semi-circular configuration as illustrated in FIG. 10 with the flat active surface shown at 32.

In the embodiment described above, the active electrode ends 16 extend straight out parallel to the rigid tube axis. In the embodiment illustrated in FIGS. 11-13, the active electrode ends are shown at 50 connected as before to an extended link 52. The bipolar active electrode ends not only spread apart (not shown) as they are extended but also angle off to the left as shown at 50. They could just as easily angle off to the right if desired. This bending action is similar to that obtained with the handpiece of the referenced patents and is obtained by simply pre-bending the electrodes so that upon their release from the confining action of the rigid tube, they will automatically spread apart as well as angle off to the side as indicated.

As in the referenced patents/application, when the tissue has been grasped, then the surgeon can apply to the tissue via the electrode ends electrosurgical currents by the usual footswitch connected to a conventional electrosurgical generator 60 (FIG. 1), also available from Elliquence LLC of Oceanside, N.Y.

While the instrument of the invention is especially useful for spinal procedures, it is not limited to such uses and it will be understood that it can be employed in any electrosurgical procedure employing a cannula in MIS.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:
1. An electrosurgical handpiece comprising:
 (a) a first main body,
 (b) a second main body axially aligned with and coupled to the first main
 (c) a squeezable handle connected to the first and second main bodies such that, when the handle is unsqueezed, the first and second main bodies assume a first relaxed position relative to one another, and when the handle is fully squeezed, the first and second main bodies assume a second fully squeezed position relative to one another, and when the handle is partially squeezed, the first and second main bodies assume a third partially squeezed position relative to one another, (d) a first tubular member having a distal end and a second end connected to one of the first and second main bodies, (e) a bipolar electrosurgical electrode comprising active separable distal ends and connecting link sections connected to the other of the first and second main bodies and extending within the tubular member, the distal ends having straight portions that are parallel to each other providing parallel facing surfaces, the straight portions terminating at their extreme respective ends in tips, characterized in that:

(f) the active distal ends and their connecting link sections are configured such that:
  i) when the handle is unsqueezed and the first and second main bodies assume their first position, the active distal ends protrude from the distal end of the first tubular member and are adjacent and parallel to and in full contact with one another, wherein the link sections are angled such that the link sections and the distal end of the tubular member form an enclosed aperture, and
  ii) when the handle is fully squeezed and the first and second main bodies assume their second position the active distal ends are fully extended outwardly from the first tubular member and the active distal ends spread apart and separate but still remain essentially parallel, and
  iii) when the handle is relaxed but still partially squeezed and the first and second main bodies assume their third position, the active distal ends being angled such that the active distal ends come together and touch first at the tips at their extreme ends and as the handle continues to relax then touch over a broader area of the distal ends in a position to grasp tissue for receiving electrosurgical currents;

(h) wherein each of the link sections comprises:
  i) an axis defined by the first tubular member
  ii) a longer straight section connected to the one of the first or second main bodies, wherein the longer straight section extends from the one of the first or second main bodies to an end of the longer straight section, wherein the end of the longer straight section is positioned a greater distance away from the axis than the respective one of the first or second main bodies;
  iii) a short angled section connecting the one of the straight portions to the end of the longer straight section, wherein the short angled section connects to one of the distal ends at a second end of the longer straight section, wherein the second end and the one of the straight portions are closer to the axis than the end of the longer straight section;
  iv) whereby the longer straight section and the second section act to keep the straight portions parallel when the handle is fully squeezed and keep the straight portions pressed together when the handle is unsqueezed; and
  v) whereby the active distal ends are angled when in the handle is relaxed but still partially squeezed such that the active distal ends come together and touch first at the tips at their extreme ends and as the handle continues to relax then touch over a broader area of the distal ends in a position to grasp tissue for receiving electrosurgical currents.

2. An electrosurgical handpiece as set forth in claim 1, wherein the first tubular member is rigid, and the active distal ends extend straight outwardly in line with the first rigid tubular member when the handle is fully squeezed.

3. An electrosurgical handpiece as set forth in claim 1, wherein the first tubular member is rigid, and the active distal ends extend outwardly and are bent at an angle to the first rigid tubular member when the handle is fully squeezed.

4. An electrosurgical handpiece as set forth in claim 1 wherein the active distal ends comprise straight portions with facing flat surfaces.

5. An electrosurgical handpiece as set forth in claim 4, wherein the link sections following the active distal ends comprise short straight portions angled outwardly relative to the distal ends and to each other.

6. An electrosurgical handpiece as set forth in claim 5, wherein the link sections following the short straight portions comprise longer straight portions angled inwardly relative to the distal ends and to each other.

7. An electrosurgical handpiece as set forth in claim 4, wherein the first tubular member is rigid, and the link sections bear against the inside surface of the rigid tubular member when the first and second main bodies assume their first position.

8. An electrosurgical handpiece as set forth in claim 4, wherein the first tubular member is rigid, and the link sections following the short straight portions comprise long straight portions angled inwardly relative to the distal ends and to each other bearing against the inner surface of the rigid tubular member when the first and second main bodies assume their first position.

9. The electrosurgical handpiece of claim 1 in combination with an RF generator generating high frequency currents at a frequency of about 4 MHz.

10. An electrosurgical handpiece comprising:
(a) a first main body,
(b) a second main body axially aligned with and coupled to the first main body,
(c) a squeezable handle connected to the first and second main bodies such that, when the handle is unsqueezed, the first and second main bodies assume a first relaxed position relative to one another, and when the handle is fully squeezed, the first and second main bodies assume a second fully squeezed position relative to one another, and when the handle is partially squeezed, the first and second main bodies assume a third partially squeezed position relative to one another,
(d) a first tubular member having a distal end and a second end connected to one of the first and second main bodies,
(e) a bipolar electrosurgical electrode comprising active separable distal ends and connecting links connected to the other of the first and second main bodies and extending within the tubular member, the distal ends having straight end portions that are parallel to each other providing electrically bare parallel facing surfaces, the straight portions terminating at their extreme respective ends in tips,
characterized in that:
(f) the connecting links back of the straight end portions comprise a short angled section followed by a longer straight section,
(g) the active distal ends and their connecting links are further configured such that:

i) when the handle is unsqueezed and the first and second main bodies assume their first position, the active distal ends and a portion only of the connecting links protrude from the distal end of the first tubular member and the straight end portions are adjacent and parallel to and in full contact position with one another, wherein the connecting links are angled such that the connecting links and the distal end of the tubular member form an enclosed aperture, and ii) when the handle is fully squeezed and the first and second main bodies assume their second position the active distal ends and connecting links are fully extended outwardly from the first tubular member and the active distal ends spread apart and separate but still remain essentially parallel, and iii) when the handle is relaxed but still partially squeezed and the first and second main bodies assume their third position, the connecting links withdrawing into the tubular member by contact with the tubular member walls forces the active distal ends to come together and touch first at the tips at their extreme ends and as the handle continues to relax and the connecting links withdraw further into the tubular member the tubular member walls force the distal ends toward their full contact position over a broader area in a position to ensure that grasped tissue by the tips is not squeezed out while receiving electrosurgical currents;

(h) wherein each of the link sections comprises:
  i) an axis defined by the first tubular member
  ii) the longer straight section connected to the one of the first or second main bodies, wherein the longer straight section extends from the one of the first or second main bodies to an end of the longer straight section, wherein the end of the longer straight section is positioned a greater distance away from the axis than the respective one of the first or second main bodies;
  iii) the short angled section connecting the one of the straight portions to the end of the longer straight section, wherein the short angled section connects to one of the distal ends at a second end of the longer straight section, wherein the second end and the one of the straight portions are closer to the axis than the end of the longer straight section;
  iv) whereby the longer straight section and the second section act to keep the straight portions parallel when the handle is fully squeezed and keep the straight portions pressed together when the handle is unsqueezed; and
  v) whereby the active distal ends are angled when in the handle is relaxed but still partially squeezed such that the active distal ends come together and touch first at the tips at their extreme ends and as the handle continues to relax then touch over a broader area of the distal ends in a position to grasp tissue for receiving electrosurgical currents.

11. An electrosurgical handpiece as claimed in claim 10, wherein the parallel facing surfaces are flat and electrically bare, and the short angled section extends at an angle of about 45° to the distal ends.

12. An electrosurgical handpiece as claimed in claim 11, wherein the longer straight section extends at an angle of about 9° to the axis of the bodies.

13. An electrosurgical handpiece comprising:
(a) a first main body (14),
(b) a second main body (20) axially aligned along a longitudinal axis with and spring-loaded (21) apart to the first main body;
(c) a squeezable handle (24,26) connected to the first and second main bodies such that, when the handle is unsqueezed, the first and second main bodies assume a first relaxed position relative to one another, and when the handle is fully squeezed, the first and second main bodies assume a second fully squeezed position relative to one another, and when the handle is partially squeezed, the first and second main bodies assume a third partially squeezed position relative to one another,
(d) a first tubular member (12) having a distal end and a second end connected to one of the first and second main bodies,
(e) a bipolar electrosurgical electrode (16) for receiving electrosurgical currents and comprising active separable distal ends (30) and connecting links (34, 36) connected to the other of the first and second main bodies and extending within the tubular member (12), the distal ends having straight end portions (30) that are parallel to each other providing electrically-bare parallel facing surfaces (32), the straight end portions (30) terminating at their extreme respective ends in tips (40),
(f) the connecting links immediately back of the straight end portions (30) comprise a short angled section (34) followed by a longer straight section (36),
(g) the active distal ends (30) and their connecting links (34, 36) are further configured such that:
  i) when the handle is unsqueezed and the first and second main bodies assume their first position, the active distal ends (30) and a portion only of the connecting links protrude from the distal end of the first tubular member (12) and the straight end portions (30) are adjacent and parallel to one another and their facing surfaces are in full contact position with one another, wherein the link sections are angled such that the link sections and the distal end of the tubular member form an enclosed aperture, and
  ii) when the handle is fully squeezed and the first and second main bodies assume their second position the active distal ends (30) and connecting links (34, 36) are fully extended outwardly from the first tubular member (12) and the active distal ends (30) spread apart and separate but still remain essentially parallel, and
  iii) as the handle is relaxed from its fully squeezed position but still partially squeezed and the first and second main bodies assume their third position, the connecting links (34, 36) while withdrawing into the tubular member (12) by contact with the tubular member walls forces the active distal ends (30) to come together and touch first at the tips (40) at their extreme ends and as the handle continues to relax and the connecting links continue to withdraw further into the tubular member (12) the tubular member walls force the distal ends (30) toward their full contact position with their facing surfaces (32) together over a broader area in a position to ensure that grasped tissue by the tips (40) is not squeezed out when and while receiving electrosurgical currents;
(h) wherein each of the link sections comprises:
  i) an axis defined by the first tubular member
  ii) the longer straight section connected to the one of the first or second main bodies, wherein the longer straight section extends from the one of the first or second main bodies to an end of the longer straight section, wherein the end of the longer straight section is positioned a greater distance away from the axis than the respective one of the first or second main bodies;

iii) the short angled section connecting the one of the straight portions to the end of the longer straight section, wherein the short angled section connects to one of the distal ends at a second end of the longer straight section, wherein the second end and the one of the straight portions are closer to the axis than the end of the longer straight section;

iv) whereby the longer straight section and the second section act to keep the straight portions parallel when the handle is fully squeezed and keep the straight portions pressed together when the handle is unsqueezed; and (v) whereby the active distal ends are angled when in the handle is relaxed but still partially squeezed such that the active distal ends come together and touch first at the tips at their extreme ends and as the handle continues to relax then touch over a broader area of the distal ends in a position to grasp tissue for receiving electrosurgical currents.

14. An electrosurgical handpiece as claimed in claim 13, wherein the parallel facing surfaces (32) are flat and electrically bare, the short angled section (34) extends outwardly at an angle of about 45° to the active distal ends, and the longer straight section (36) extends back toward the longitudinal axis at an angle of about 9° to the longitudinal axis of the bodies.

15. An electrosurgical handpiece as claimed in claim 14, wherein the active distal ends have a semi-circular configuration.

16. An electrosurgical handpiece as claimed in claim 14, further comprising an extended link (52) connected to the active distal ends (30) to cause the latter to angle off the longitudinal axis as the first and second main bodies assume their second position.

* * * * *